(12) United States Patent
Wohltjen et al.

(10) Patent No.: US 7,449,050 B2
(45) Date of Patent: Nov. 11, 2008

(54) SYSTEM, APPARATUS AND METHOD FOR CONCENTRATING CHEMICAL VAPORS

(75) Inventors: Henry Wohltjen, Bowling Green, KY (US); Mark Klusty, Smiths Grove, KY (US)

(73) Assignee: Microsensor Systems, Inc., Bowling Green, KY (US)

( * ) Notice: Subject to any disclaimer, the term of this patent is extended or adjusted under 35 U.S.C. 154(b) by 432 days.

(21) Appl. No.: 11/321,824

(22) Filed: Dec. 29, 2005

(65) Prior Publication Data

US 2007/0151449 A1 Jul. 5, 2007

(51) Int. Cl.
*G01N 1/22* (2006.01)
*G01N 1/40* (2006.01)

(52) U.S. Cl. .............................. 95/148; 96/112; 96/116; 96/146; 96/413; 73/31.07; 73/863.12; 73/863.21; 422/88; 436/178

(58) Field of Classification Search .................... 95/90, 95/148; 96/108, 112, 115, 116, 146, 413; 73/23.2, 31.01, 31.07, 863.11, 863.12, 863.21; 422/88; 436/178
See application file for complete search history.

(56) References Cited

U.S. PATENT DOCUMENTS

| | | | |
|---|---|---|---|
| 4,046,014 A | 9/1977 | Boehringer et al. | |
| 4,293,316 A | 10/1981 | Block | |
| 4,350,037 A * | 9/1982 | Higham | 73/23.39 |
| 4,759,210 A | 7/1988 | Wohltjen | |
| 4,805,441 A | 2/1989 | Sides et al. | |
| 5,014,541 A * | 5/1991 | Sides et al. | 73/23.41 |
| 5,142,143 A * | 8/1992 | Fite et al. | 250/288 |
| 5,391,358 A * | 2/1995 | Heim | 422/171 |
| 5,611,846 A | 3/1997 | Overton et al. | |
| 6,223,584 B1 | 5/2001 | Mustacich et al. | |
| 6,354,160 B1 | 3/2002 | Staples et al. | |
| 6,837,118 B2 * | 1/2005 | Bonne et al. | 73/863.12 |

FOREIGN PATENT DOCUMENTS

| | | |
|---|---|---|
| EP | 0525950 | 2/1993 |
| WO | 01/36934 | 5/2001 |

OTHER PUBLICATIONS

International Search Report issued for International Application No. PCT/US2006/028093, Dec. 18, 2006.

(Continued)

*Primary Examiner*—Frank M Lawrence
(74) *Attorney, Agent, or Firm*—Kramer Levin Naftalis & Frankel LLP (57) ABSTRACT

An apparatus for concentrating a vaporous substance, which comprises: a sorbent material capable of capturing a vaporous substance; a first housing in which the sorbent material is located, a heating element proximate the exterior of the housing; a second housing defining a chamber within which the first housing resides, the first housing being located in said chamber such that there is a space permitting gas flow between the outside of the first housing and the inside of the second housing; and a pump capable of causing an exhaust gas to flow through the space in contact with the outside of the first housing; and methods for making and utilizing such apparatus.

23 Claims, 3 Drawing Sheets

OTHER PUBLICATIONS

Chia-Jung Lu et al "A Dual-Adsorbent Preconcentrator for a Portable Indoor-VOC Microsensor System", Analytical Chemistry, vol. 73, No. 14, Jul. 15, 2001, pp. 3449-3457.

Grate et al., "Smart Sensor System for Trace Organophosphorous and Organosulfur Vapor Detection Employing a Temperature-Controlled Array of Surface Acoustic Wave Sensors, Automated Sample Preconcentration, and Pattern Recognition", *Analytical Chemistry*, 1993, 65, pp. 1868-1881.

Bender et al., "Development of a preconcentration unit for a SAW sensor micro array and its use for indoor air quality monitoring," *Sensors & Acutators B: Chemical*, vol. 93, Issues 1-3, Aug. 2003, pp. 135-141.

Neiβ et al., "A miniaturized themal desportion unit for chemical sensing below the odor threshold," *Sensors & Acutators B: Chemical*, vol. 95, Issues 1-3, Oct. 2003, pp. 1-5.

* cited by examiner

SYSTEM, APPARATUS AND METHOD FOR CONCENTRATING CHEMICAL VAPORS

FIELD OF THE INVENTION

The invention relates to technology for concentrating vaporous substances for improved detection by a sensing instrument.

BACKGROUND OF THE INVENTION

Detection devices and monitoring and measurement instruments are frequently used for ascertaining the presence and concentration of selected gaseous chemical species in a subject environment. Unfortunately, in many instances, the concentration of the gas or vapor of interest may fall below the effectiveness floor of the technology in question. To address this situation, the art has devised various techniques for the concentration, or enrichment, of the gas or vapor species such that, if the species is present, it can be collected to accumulate its concentration to a level above the detection threshold of the particular technology being utilized.

One attractive conventional enrichment technique involves the use of a vapor sorbent material that serves to sorb (or "trap") the vapor. If the sorbent material is exposed to a large volume of the vapor from the subject environment, a significant mass of the desired vapor will accumulate in or on the sorbent material. The sorbent material is then subjected to conditions which cause release of the vapor, thereby providing a collected sample of the vapor species. If the process of releasing the vapor species from the sorbent material can be accomplished in a relatively short period of time, a significant increase in the concentration of the target vapor is attained.

For example, in an apparatus for implementing this technique, vapor sorbent material is held in a tubular container. A gaseous sample is then passed through the container, wherein the vapor (if present) is trapped by the sorbent material. The container is then heated, thereby releasing a concentrated sample of the vapor, which is provided to an instrument (for example, a gas chromatograph) for analysis. Thereafter, a cooling device is used to restore the container to its starting temperature, at which time a new absorption-heating-cooling cycle can be commenced. Typically, glass wool or another wadding material is used to position the sorbent material in the container and prevent the sorbent material from moving out of its position near the heating source. However, several difficulties are associated with such apparatus.

First, the wadding material utilized to position the sorbent material does not reliably protect it against imprecise positioning (including shifting) in the vapor concentrator container, and the efficiency of the system will suffer in several respects. More specifically, imprecise positioning of the sorbent material with respect to the heating source will result in the need for extra heat and energy to attain the temperature of the sorbent material necessary for the desired rate of desorption. Consequently, the efficiency of the system will suffer as additional expenditure of energy and/or time will be required to reach the desired level of performance. Further, imprecise positioning of the wadding material can compromise the effectiveness of the vapor sorption and desorption process, leading to corresponding unpredictability in the rates of sorption and desorption of vapor species, and an inability to replace a sorbent material with one that performs comparably.

Second, the wadding material itself can interfere with the efficiency of the process. Typically, glass wool or other porous wadding material is placed in the tubular flow path of the container to maintain the positioning of the sorbent material in proximity to the heating source. While the wadding material allows the passage of vapors, it can also act as a sorbent. Thus, the wadding material must be heated to prevent high molecular weight vapors from adhering to it.

Third, a separate cooling device is generally used to assist in returning the vapor concentrator to its starting temperature, representing an additional source of power consumption. For example, the cooling device typically consists of a fan, a device that is unattractive for use in a low power system especially one having a compact design. In the alternative, passive cooling is sometimes utilized to achieve a return to the concentrator's starting temperature, but this tends to be a limited cooling solution which can extend the time necessary for the apparatus to complete a full absorption-heating-cooling cycle.

Because of the drawbacks attendant upon the above-mentioned approaches, provision of technology for securing a concentrated vapor sample, which technology is not similarly afflicted, would be a significant advance.

OBJECTS OF THE INVENTION

It is an object of the invention to provide apparatus and a method for generating a concentrated amount of a vapor chemical species collected from a target environment.

It is another object of the invention to provide apparatus and a method for generating a concentrated amount of a vapor chemical species collected from a target environment, which concentrated amount is suitable for detection by chemical sensor devices.

It is yet another object of the invention to provide compact apparatus for generating concentrated amounts of a vapor chemical species as well as a method involving same.

It is a further object of the invention to provide apparatus for generating concentrated amounts of a vapor chemical species that has minimal power requirements and improved speed of operation, as well as a method involving same.

SUMMARY OF THE INVENTION

In one aspect, the invention is an apparatus for concentrating a vaporous substance, which comprises: a sorbent material capable of capturing said vaporous substance; a first housing in which the sorbent material is located, which housing is metallic and has an inlet port and an outlet port, said housing being fitted with a heating element proximate the exterior of the housing, which heating element is capable when activated of delivering an amount of heat energy to a zone within the interior volume of the housing, the amount of said heat energy being sufficient to effect release of said substance captured by the sorbent material; at least one metallic screen element welded to the interior surface of said first housing, said at least one screen element holding the sorbent material in position within the housing between the inlet and outlet ports and in said zone; a second housing defining a chamber within which the first housing resides, the first housing being located in said chamber such that there is a space permitting gas flow between the outside of the first housing and the inside of the second housing, the second housing being configured such that the volume between the first housing and the second housing is no more than the volume within the first housing; and a pump, the intake of which is interconnected with the interior volume of said first housing, such that when the pump is activated gas possibly containing said vaporous substance is caused to flow through the inlet port and to come in contact with the sorbent material, and the exhaust of which is interconnected with the space between the first housing and the second housing, such that when the pump is activated the exhaust gas therefrom is caused to flow through the space in contact with the outside of the first housing.

In another aspect, the invention is a method of concentrating a vaporous substance which comprises: inducing, via the action of a pump, gas which may contain said substance to contact a sorbent material capable of capturing said substance, said sorbent material being located within a first housing which is metallic and has an inlet port and an outlet port, and being held in position within the housing between the inlet port and the outlet port by at least one metallic screen element welded to the interior surface of said housing; after a period of time during which the gas and the sorbent material have been in contact, subjecting a zone within the interior volume of said housing, in which zone the sorbent material resides, to an amount of heat sufficient to release from said sorbent material any of said substance captured thereby; contacting said first housing with exhaust gas from said pump such that heat is removed from said zone and from the sorbent material residing therein, and the sorbent material is restored to a condition in which it can capture said substance.

In still another aspect, the invention is a method of forming a vapor concentrator, which comprises: welding at least one metallic screen element to the interior surface of a first housing which is metallic, has an inlet port and an outlet port and is fitted with a heating element proximate the exterior of said first housing, such that when a sorbent material is located abutting said at least one metallic screen said material is in a zone wherein the material is subjected to heat energy generated by the heating element when said element is activated; locating the sorbent material within said first housing and abutting said at least one metallic screen such that the sorbent material is retained in position between said inlet and outlet ports and in said zone; positioning said first housing within a second housing such that there is a space permitting gas flow between the outside of the first housing and the inside of the second housing; interconnecting the interior volume of said first housing with a pump such that when the pump is activated a gas possibly containing the vaporous substance is caused to flow through the inlet port, and to come in contact with the sorbent material; and interconnecting the space between the outside of the first housing and the inside of the second housing with the exhaust of said pump such that when the pump is activated the exhaust gas therefrom is caused to flow through said space in contact with the outside of the first housing.

Practice of the invention results in substantial advantages. The invention is useful for generating a concentrated sample of any of a broad spectrum of vapors. In addition, the invention is able to generate concentrated vapor samples with a high energy efficiency and speed of operation, allowing the performance of multiple, repetitive measurements, to provide the user with more data on the target environment conditions over a specified time period. Practice of the invention is furthermore very economical in terms of space requirements, allowing the invention to be offered in a portable, handheld device. Moreover, by utilizing a high efficiency design with minimal power consumption requirements, the life of the apparatus' power source can be extended, thereby minimizing maintenance. Also, the design of the invention allows the generation of consistent, and therefore predictable, concentrated vapor samples.

DESCRIPTION OF CERTAIN PREFERRED EMBODIMENTS

As indicated above, an important goal of the invention is provision of a concentrated vapor sample suitable for detection and or analysis by a chemical detection instrument in a simple, efficient and repeatable manner. Central features of the invention, which enable attainment of such goal include a metal or metal alloy screen element to retain the sorbent material in a good position for sorbing any vapor of interest present, attachment of each screen element via welding to a desired position on the interior surface of a housing within which the sorbent material is contained, utilization of a housing made from a suitable metal or metal alloy, and cooling of the sorbent material rising exhaust gas from a pump that causes gas flow through the housing interior.

For purposes of energy efficiency, it is preferred that as many as practical of the components of the device be constructed of metal or metal alloy. It is particularly important for the housing enclosing the sorbent material and the components contained therein. The use of high conductivity metallic components (i.e., of metal or a metal alloy) increases heat transfer from the heating element to the sorbent material, resulting in a faster, more energy efficient heating stage.

During the cooling stage, while the desired direction of heat transfer is reversed, the advantages of using high conductivity metal components are equally applicable, as high conductivity metal components are more efficient at removing heat from the housing enclosing the sorbent material and the contents therein. In addition to the components in the region of the housing, the use of metal components in other regions of the apparatus aids in cooling. For example, the use of metal tubing for conduits interconnecting the housing chamber, the pump, and the space in proximity of the housing's exterior results in the passive cooling of the gas as it flows through the conduits on route to such space. (There may also be a cooling effect as the gas flows through the analysis instrument and pump if heat is transferred to the housings of those components.)

While the invention is suitable for use in any of a number of different concentration applications, as will be apparent to those ordinarily skilled in the art once in possession of the technique herein, it is especially advantageous for utilization with chemical vapor detection instruments. These are used in a wide variety of areas, including the chemical, government, medical, food and beverage, semiconductor, automotive, pharmaceutical and petroleum markets. Some examples include detection instruments and technologies based on bulk and surface acoustic wave sensor and arrays, gas chromatographs, chemiresistor sensors and arrays and electrochemical cell array sensors and arrays.

A principal thrust of the invention is to facilitate the detection (i.e., sensing of the presence or amount) of chemical species when the concentration of the target chemical species (if there at all) in the ambient environment may fall below the detection limits of the sensor technology. The invention is superior to other concentration units currently used with many chemical vapor detection instruments—which units feature a sorbent material that sorbs vapors from a gaseous sample pulled through the concentration unit by the action of a pump and then releases the sorbed species when the sorbent material is subjected to appropriate conditions, typically heat, the sorbent material thereafter being allowed to cool to its initial temperature so that the absorption-heating-cooling cycle can be initiated again—because with the invention the efficiency and reliability of the sorption, heating and cooling functions is substantially increased. This is a result, inter alia, of the accuracy and permanence of positioning the sorbent material via at least one weld-secured metallic screen element (the use of welded metal components adds a level of ruggedness to the apparatus and results in a minimization or elimination of movement of and between components), the utilization of metal or metal alloy materials that conduct heat, and the provision of a relatively fast and compact cooling function.

Figure 1:
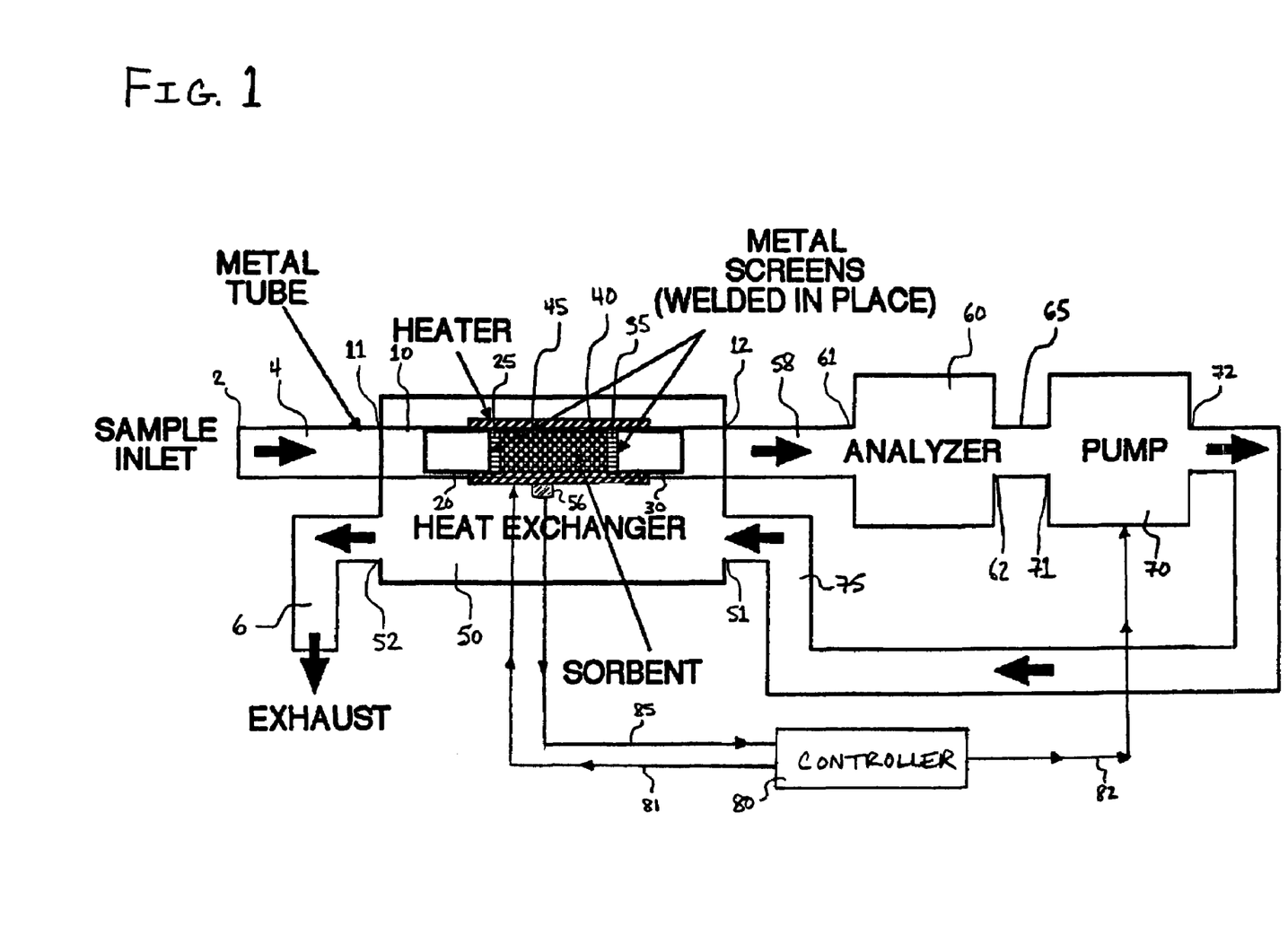
FIG. 1 is a schematic diagram showing an embodiment suitable for chemical vapor concentrating according to the present invention.

Thus, in accordance with FIG. 1, a preferred embodiment of the invention comprises a sample inlet 2, a first enclosure (i.e., housing) 10 containing a sorbent material 45, metallic screen 25 and metallic screen 35 abutting the sorbent material and welded in place, a heating element 40 in thermal contact with housing 10, an analysis instrument 60 connected to housing 10, a pump 70 interconnected with the analysis instrument, and a second enclosure (i.e., housing) 50 encompassing housing 10 and connected to the pump and an outlet conduit 6.

More specifically, in the embodiment depicted in FIG. 1, the chamber within housing 10 is in communication via port 11 with inlet conduit 4, which in turn is in communication with the target environment via port 2. The chamber within housing 10, through port 12, is also in communication with conduit 58, which is also in communication with the analysis instrument 60 via port 61. Housing 10 is located within housing 50. Analysis instrument 60, through port 62, is in communication with conduit 65, which is interconnected with pump 70, which pump is in turn interconnected with conduit 75 via port 72. Conduit 75, through port 51, is in communication with the chamber within housing 50, which is in communication, via port 52, with outlet conduit 6.

The sorbent material 45 is located within housing 10 and held in place on one side by metallic screen 25 and on the other side by metallic screen 35. Screens 25 and 35 are preferably fabricated of a chemically inert, thermally conductive metal (e.g., stainless steel, which offers the added advantage of easy weldability). The screens should also be designed to cause minimal hold-up of trapped vapors and to offer highly predictable porosity.

Screens 25 and 35 are connected, respectively, to screen retainer tube 20 and screen retainer tube 30. Screen retainer tube 20 and screen retainer tube 30 are hollow tubular structures that are affixed (directly or indirectly) to housing 10 and serve to hold screens 25 and 35 in their respective positions. Like screens 25 and 35, housing 10 and screen retainer tubes 20 and 30 are preferably fabricated of a chemically inert, thermally conductive metal (e.g., stainless steel, which again offers the added advantage of easy weldability).

To obtain a concentrated sample of the desired vapor species, the sorption stage is commenced, in connection with which pump 70 is activated, causing a gas sample from the target environment to enter inlet port 2 and pass through conduit 4 and housing 10 such that it comes in contact with sorbent material 45, wherein the vapor species (if present) is sorbed (or "trapped"). Some common sorbent materials include Tenax TA™, Chromosorb™, Carbopack B™, Carboxen 1016™ activated charcoal, and silica gel (available commercially from companies such as Supelco and Alltech Associates, Inc.), although a multitude of other materials known in the art are also suitable.

Heating element 40 is located abutting, and in thermal contact with, housing 10. When the user desires that a concentrated vapor sample be sent to analysis instrument 60, heating element 40 is activated by controller 80 via signals traveling along heating control line 81 and energized to deliver a controlled amount of heat to the volume within housing 10 with which it is in thermal contact, resulting in a temperature increase in sorbent material 45 positioned in the interior of housing 10. As sorbent material 45 is heated, the vapor species concentrated sorbed there on desorbs for transport to the instrument. After the desired amount of heating is accomplished, heating element 40 is deactivated. The concentrated vapor sample is then drawn by the action of pump 70 to analysis instrument 60. Analysis instrument 60 is a surface acoustic wave array device (though, as indicated in a preceding paragraph, it can alternatively be a gas chromatograph, electrochemical cell array detection instrument, chemiresistor device or array, or any other suitable chemical vapor detection instrument).

The amount of heat delivered by heating element 40 can be controlled in three or more different ways. In the FIG. 1 embodiment, it operates to provide heat energy for a set interval of time. The amount of delivered heat energy is calculable using the voltage and efficiency of the heating element and duration of the heating stage. After the desired period of time has elapsed, controller 80 sends an appropriate deactivation signal to the heating element 40 and the heating cycle is arrested. Alternatively, data on the temperature at or in the vicinity of housing 10 (including without limitation the volume within the housing) can be provided by sensor 56 though temperature feedback line 85. When the desired temperature is reached, controller 80 sends an appropriate deactivation signal to the heating element 40.

When (assuming the target species is present) a concentrated sample has been desorbed and sent to analysis instrument 60, and heating element 40 deactivated, the cooling stage begins. All gas passing through housing 10, instrument 60, and pump 70 is fed to the chamber within housing 50 and exhausted through outlet conduit 6. Housing 50, pump exhaust gas flowing through its interior volume, and housing 10 positioned therein, combine to function as a heat exchanger that removes heat energy created by heating element 40 during the heating stage. Preferably, the size of housing 50 and the volume within are minimized to affect better heat transfer. More specifically, if such volume is decreased, gas traveling through housing 50 and around housing 10 is on average in closer proximity to the surface of housing 10, thus better effecting heat transfer to the gas for removal.

There are several modes of pump operation that can be adopted during the sorption, heating, and cooling stages. In the simplest mode, pump 70 can be operated continuously and at a constant speed. The pump draws sample gas from the target environment into inlet port 2 and the interior volume of housing 10 during the sorption stage, draws concentrated vapor to analysis instrument 60 during and/or after the heating stage, and pushes exhaust gas through the space between housing 10 and housing 50 during the cooling stage. One of the benefits of continuous operation of the pump is simplicity of operation and the reduction of any repetitive stress that may result from on-and-off cycling of the pump.

Alternatively, the pump can be intermittently activated, and (when on) its action level varied, via transmission of appropriate signals from controller 80 along pump control signal line 82 during certain stages of operation. As it is desirable that concentrated vapor be released into a smaller volume in order to protect against dilution, it is advantageous that the operation of pump 70 be halted (or eased) during the heating phase to limit the amount of gas passing through housing 10 and sorbent material 45. By significantly or completely reducing flow during the heating phase, a more concentrated vapor sample is available for delivery to analysis instrument 60. When the heating stage is complete, a signal is sent by controller 80 through pump control signal line 82 instructing pump 70 to resume (or increase) flow and the concentrated sample is transported for analysis.

Varying, or "pulsing," the speed or operation of the pump is quite advantageous. First, and most obvious, as the pump is not operating continuously, there is an overall reduction in the amount of energy over a cycle of operation. Correlatively, the amount of heat energy required to obtain a concentrated sample is reduced, as flow is reduced at the desorption site, the amount of desorbed vapor swept from the site by the action of the pump will be reduced, and thus the length of heating stage (and the requisite amount of heat energy) can be reduced as the desorbed concentrated vapor will be retained at the desorption site until the pump is reactivated. Additionally, reducing the action of the pump during the heating stage correspondingly reduces gas flow through the second enclosure, which gas flow could otherwise sap heat from the heating element and thus hamper its efficiency. On the whole, this "pulse" mode of operation results in better energy efficiency and lower power consumption, which is especially important for embodiments of the invention comprising a portable, handheld device.

An electrically activated heater and an electrically controlled pump are preferably utilized. Controller 80 is a processor (e.g., a microcomputer) that governs the amount of heat delivered by activating, and thereafter deactivating, heating element 40, as described supra. Sensor 56 is preferably an electrical temperature sensing device (for example, a thermocouple or thermistor); however, the sensor can alternatively be any device capable of delivering a temperature feedback signal to the controller 80. Likewise, the action of pump 70 is controlled by a processor. In the preferred embodiment, the controller 80 electrically controls the operation of pump 70 by sending signals to the pump over pump control signal line 82.

Figure 2:
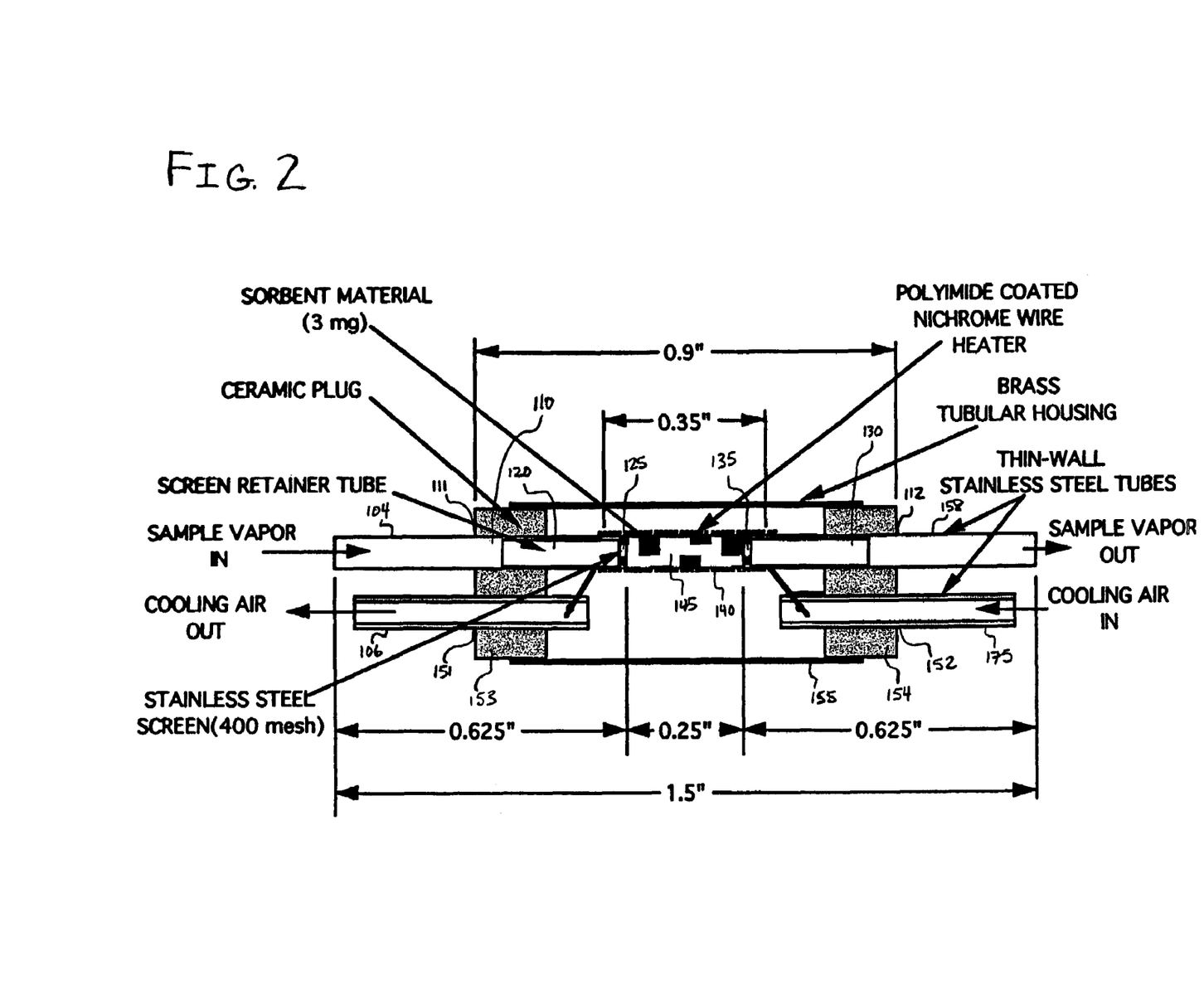
FIG. 2 is a schematic diagram showing an embodiment of a concentrator including a heat exchanger according to the present invention.

In FIG. 2, a preferred embodiment of the first housing and second housing of the apparatus (with component dimensions) is shown. While the invention is suitable for use in a compact, low power consumption device, there are no particular size limits to the apparatus. However, by minimizing the mass of sorbent material and the volume of the associated gas flow paths, the amount of energy required to operate the apparatus is reduced and power consumption optimized.

In this preferred embodiment, the first housing 110 consists of a thin walled stainless steel tube having an outside diameter of 0.065 inches and a length of 0.9 inches. First housing 110 has a polyimide coated nichrome heater wire 140 wrapped around its outside diameter, extending over a 0.35 inch length of the enclosure. The lateral location of heater wire 140 with respect to enclosure 110 defines the desired location of the sorbent material bed 145 within the first housing. The sorbent bed contains approximately 2 to 8 milligrams of sorbent material (e.g., Tenax TA, Chromosorb 106, Carbopack B, Carboxen 1016, activated charcoal).

Metal screen 125 and metal screen 135 hold the sorbent in place and consist of small disks that are approximately the same size as the inner diameter of first housing 110 and are fabricated from 400 mesh stainless steel. These metal screens are respectively spot-welded onto the end of screen retainer tube 120 and screen retainer tube 130, which consist of stainless steel tubes approximately 0.25 inches long and with an outside diameter slightly smaller than the internal diameter of the first housing 110.

First housing 110 and the components contained therein are fabricated by inserting screen retainer tube 120 (and attached metal screen 125) into the first housing 110. Once metal screen 125 is in its desired location approximately half the predicted length of the sorbent bed from the medial point of the first housing 110, it is then spot-welded using a brief high current electrical discharge between screen retainer tube 120 and first housing 110. The desired amount of sorbent material 145 (weighed using an analytical balance) is then "loaded" into the first housing 110 by drawing it into the first enclosure with the aid of a vacuum pump. Screen retainer tube 130 is subsequently inserted into the open end of the first enclosure, pressed against the sorbent material until it is "packed" to the desired density, and similarly spot-welded to first housing 110.

First housing 110 is then placed inside the larger diameter second housing 150, a sealed chamber consisting of a larger brass tube 155 of a 0.35 inch internal diameter bounded at the ends by ceramic spacer 153 and ceramic spacer 154, both of a slightly smaller 0.325 inch outer diameter. Both ceramic spacer 153 and ceramic spacer 154 feature a pair of 0.065 inch diameter holes, corresponding to ports 111, 112, 151, and 152. The respective ends of the first housing 110 are placed into the holes of the ceramic spacer 153 and ceramic spacer 154 corresponding to port 111 and port 112, respectively, and attached using an adhesive. Stainless steel conduit 175 and stainless steel conduit 106 are then placed in the remaining hole in each of the ceramic spacers (corresponding to port 151 and port 152, respectively) and likewise attached with adhesive. These conduits serve as the inlet and outlet of second housing 150 for the gas flow used to cool the first housing 110 and heating element 140.

Figure 3:
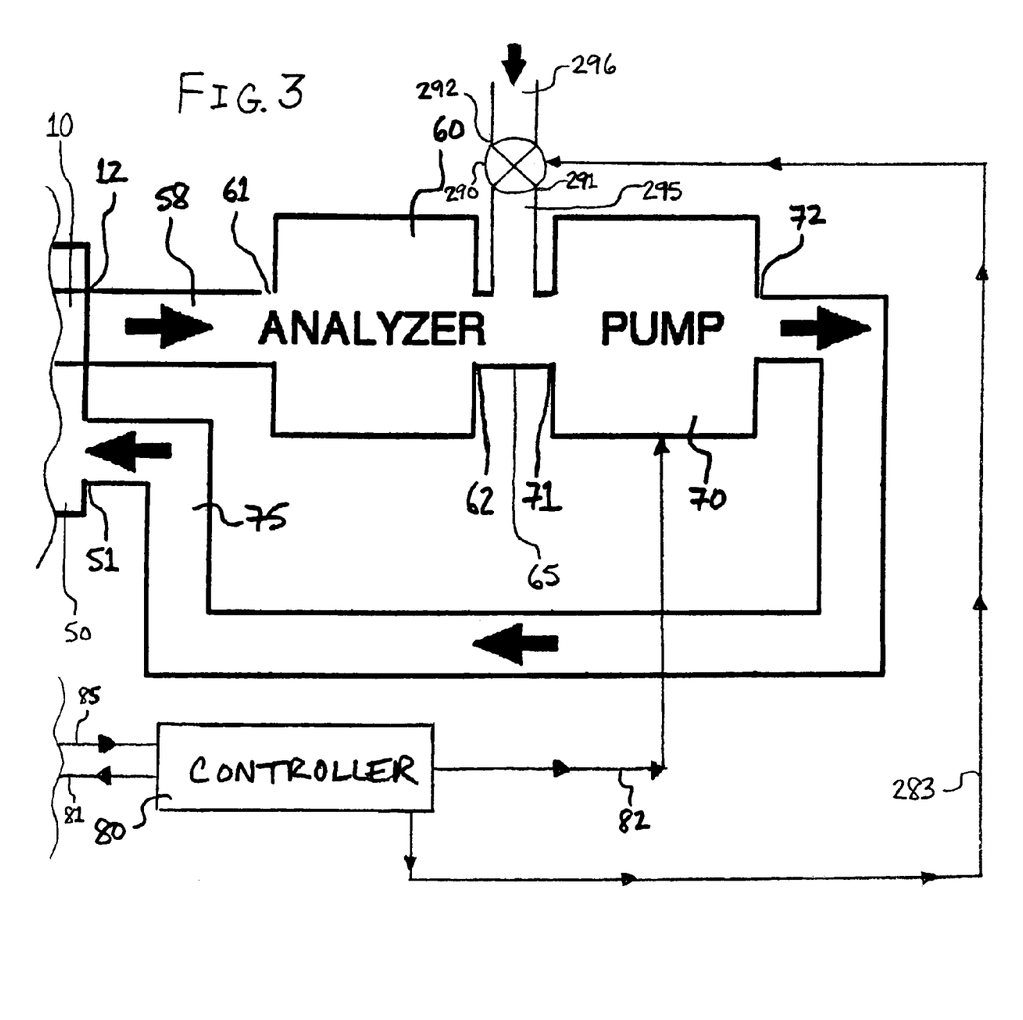
FIG. 3 is a schematic diagram showing an embodiment suitable for chemical vapor concentrating according to the present invention.

FIG. 3 shows a variation on the invention offering certain advantages. This advantageous embodiment involves the structure depicted in FIG. 3 integrated into the apparatus as otherwise depicted in FIG. 1 (certain elements of which are also shown in FIG. 3 to provide a point of reference). Thus, in FIG. 3, valve 290 is, via port 292, in communication with an inlet conduit 296. Valve 290, via port 291 and conduit 295, is similarly in communication with conduit 65, which interconnects analysis instrument 60 and pump 70. In its open position, valve 290 permits communication between inlet conduit 296 and conduit 295, and thereby communication with conduit 65. The position of valve 290 is controlled, preferably electrically, by controller 80, which sends signals to the valve via valve control signal line 283. Valve 290, in its open position, allows gas to enter from inlet conduit 296 and into conduit 65 at which time the gas is induced by pump 70 to flow into second enclosure 50, wherein the gas aids in cooling the contents of the second housing. Preferably, valve 290 is opened at the commencement of the cooling stage, during which stage it is desirable to introduce gas from the target environment, which is likely to be cooler than the gas traveling through conduit 65 from instrument 60. The introduction of cooler gas into the system increases the cooling efficiency of the apparatus and reduces the time necessary to complete the cooling stage, leading to a corresponding reduction in the combined absorption-heating-cooling time for the apparatus.

The invention described herein is susceptible of many modifications and variations within its scope, and in particular extends to the use of any one or more of the singular and several features of the foregoing description and accompanying drawings and their equivalents.

What is claimed is:

1. Apparatus for concentrating a vaporous substance, which comprises:
    a sorbent material capable of capturing said vaporous substance;
    a first housing in which the sorbent material is located, which housing is metallic and has an inlet port and an outlet port, said housing being fitted with a heating element proximate the exterior of the housing, which heating element is capable when activated of delivering an amount of heat energy to a zone within the interior volume of the housing, the amount of said heat energy being sufficient to effect release of said substance captured by the sorbent material;
    at least one metallic screen element welded to the interior surface of said first housing, said screen element holding the sorbent material in position within the housing between the inlet and outlet ports and in said zone;
    a second housing defining a chamber within which the first housing resides, the first housing being located in said chamber such that there is a space permitting gas flow between the outside of the first housing and the inside of the second housing; and
    a pump, the intake of which is interconnected with the interior volume of said first housing, such that when the pump is activated gas possibly containing said vaporous substance is caused to flow through the inlet port and to come in contact with the sorbent material, and the exhaust of which is interconnected with the space between the first housing and the second housing, such that when the pump is activated the exhaust gas therefrom is caused to flow through the space in contact with the outside of the first housing.

2. Apparatus as defined in claim 1 wherein the second housing is configured such that the volume between the first housing and the second housing is no more than the volume within the first housing.

3. Apparatus as defined in claim 1 which further comprises a processor electrically connected to the heating element, which processor is capable of activating and deactivating the heating element.

4. Apparatus as defined in claim 3, wherein the processor deactivates the heating element a predetermined time after it activates said heating element.

5. Apparatus as defined in claim 3, which further comprises a sensor that is positioned so as to be in contact with the contents of the first housing and that is capable of ascertaining the temperature of said contents, said sensor being electrically connected to the processor such that the processor receives signals therefrom permitting the processor to recognize an increase in temperature of said contents and in response to attainment of a predetermined increment of temperature increase deactivates the heating element.

6. Apparatus as defined in claim 3, wherein the processor is a microcomputer.

7. Apparatus as defined in claim 3, wherein the processor is electrically connected to the pump, which processor is capable of activating and deactivating the pump.

8. Apparatus as defined in claim 7, wherein the processor deactivates the pump a predetermined time after it activates said pump.

9. Apparatus as defined in claim 7, wherein the processor is a microcomputer.

10. Apparatus as defined in claim 1, which further comprises a valve having one port communicating with said pump and one port communicating with a vent to the ambient atmosphere, said valve being capable of alternating between its one position in which the pump and the ambient atmosphere are in communication and another position in which the valve prevents communication with the ambient atmosphere.

11. Apparatus as defined in claim 10, wherein the valve's movement from one position to another is electrically actuated.

12. A method of concentrating a vaporous substance which comprises:
    inducing, via the action of a pump, gas which may contain said substance to contact a sorbent material capable of capturing said substance, said sorbent material being located within a first housing which is metallic and has an inlet port and an outlet port, and being held in position within the housing between the inlet port and the outlet port by at least one metallic screen element welded to the interior surface of said housing
    positioning said first housing within a second housing such that there is a space permitting gas flow between the outside of the first housing and the inside of the second housing;
    after a period of time during which the gas and the sorbent material have been in contact, subjecting a zone within the interior volume of said first housing, in which zone the sorbent material resides, to an amount of heat sufficient to release from said sorbent material any of said substance captured thereby; and
    contacting said first housing with exhaust gas from said pump such that heat is removed from said zone and from the sorbent material residing therein, and the sorbent material is restored to a condition in which it can capture said substance.

13. A method as defined in claim 12 wherein the second housing is configured such that the volume between the first housing and the second housing is no more than the volume within the first housing.

14. A method as defined in claim 12, which further comprises activating and deactivating the heating element via a processor electrically connected to the heating element.

15. A method as defined in claim 14, which further comprises deactivating the heating element a predetermined time after activating it.

16. A method as defined in claim 14, which further comprises ascertaining the temperature of the contents of said first housing, by means of a sensor electrically connected to the processor such that the processor receives signals therefrom permitting the processor to recognize an increase in temperature of said contents, and deactivating the heating element in response to attainment of a predetermined increment of temperature increase.

17. A method as defined in claim 14, wherein the processor is a microcomputer.

18. A method as defined in claim 14, which further comprises activating and deactivating the pump by means of a processor electrically connected to the pump.

19. A method as defined in claim 18, which further comprises deactivating the pump a predetermined time after activating it.

20. A method as defined in claim 18, wherein the processor is a microcomputer.

21. A method as defined in claim 12, which further comprises contacting said first housing with gas from the ambient environment, the flow of which gas is regulated by a valve interconnected with the conduit running between said first housing and said pump at the same time the first housing is being contacted with exhaust gas from the pump.

22. A method of forming a vapor concentrator, which comprises:
  welding at least one metallic screen element to the interior surface of a first housing which is metallic, has an inlet port and an outlet port and is fitted with a heating element proximate the exterior of said first housing, such that when a sorbent material is located abutting said at least one metallic screen said material is in a zone wherein the material is subjected to heat energy generated by the heating element when said element is activated;
  locating the sorbent material within said first housing and abutting said at least one metallic screen such that the sorbent material is retained in position between said inlet and outlet ports and in said zone;
  positioning said first housing within a second housing such that there is a space permitting gas flow between the outside of the first housing and the inside of the second housing;
  interconnecting the interior volume of said first housing with a pump such that when the pump is activated a gas possibly containing the vaporous substance is caused to flow through the inlet port, and to come in contact with the sorbent material; and
  interconnecting the space between the outside of the first housing and the inside of the second housing with the exhaust of said pump such that when the pump is activated the exhaust gas therefrom is caused to flow through said space in contact with the outside of the first housing.

23. A method as defined in claim 22 which further comprises interconnecting a valve to the conduit running between the first housing and the pump said valve also being interconnected with the ambient environment, such that when the valve is in its open position and the pump is activated gas from the ambient environment is caused to flow through said space in contact with the outside of the first housing.

* * * * *